United States Patent

Grausz

[11] 4,026,298
[45] May 31, 1977

[54] ARTIFICIAL URETHRA

[75] Inventor: Henry Grausz, Ross, Calif.

[73] Assignee: Grausz Investment Co., San Francisco, Calif.

[22] Filed: Dec. 3, 1975

[21] Appl. No.: 637,120

[52] U.S. Cl. .................. 128/349 R; 128/DIG. 25
[51] Int. Cl.² ........................................ A61M 15/00
[58] Field of Search ....... 128/349 R, 349 B, 350 R, 128/350 V, 274, DIG. 25

[56] References Cited

UNITED STATES PATENTS

| | | | |
|---|---|---|---|
| 1,920,006 | 7/1933 | Dozier | 128/349 R |
| 2,024,982 | 12/1935 | Scott | 128/349 R |
| 2,616,429 | 11/1952 | Merenlender | 128/350 R |
| 2,687,731 | 8/1954 | Iarussi et al. | 128/349 R |
| 3,044,468 | 7/1962 | Birtwell | 128/349 B |
| 3,108,595 | 10/1963 | Overment | 128/350 R |
| 3,331,371 | 7/1967 | Rocchi et al. | 128/349 B |
| 3,642,004 | 2/1972 | Osthagen et al. | 128/349 R |
| 3,954,110 | 5/1976 | Hutchinson | 128/349 B |

Primary Examiner—Dalton L. Truluck
Attorney, Agent, or Firm—Warren, Chickering & Grunewald

[57] ABSTRACT

A urinary catheter having a pair of longitudinally-spaced passage closing means which may be individually and sequentially operated for draining the urinary bladder and when in closed position providing an air lock effectively preventing transmission of infecting agents into the bladder.

11 Claims, 5 Drawing Figures

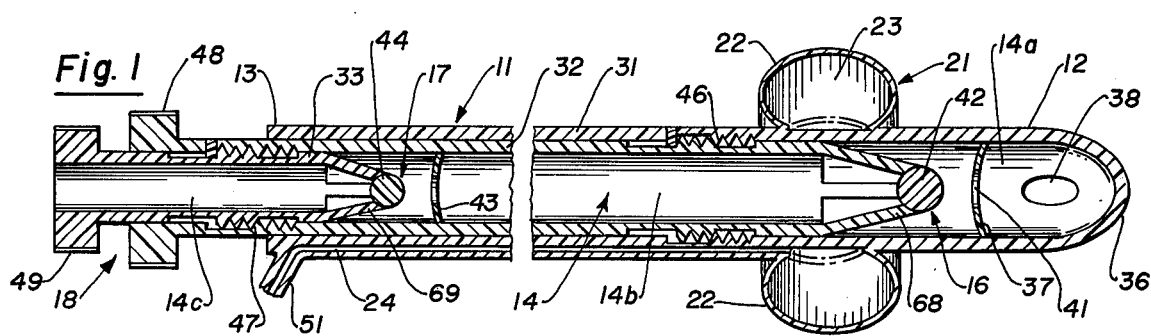
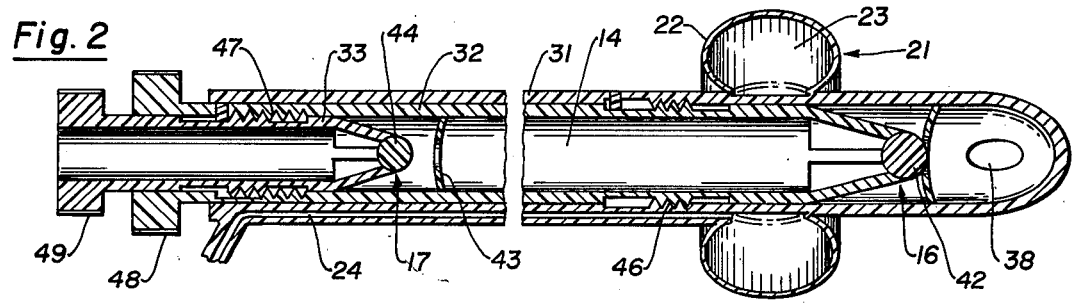
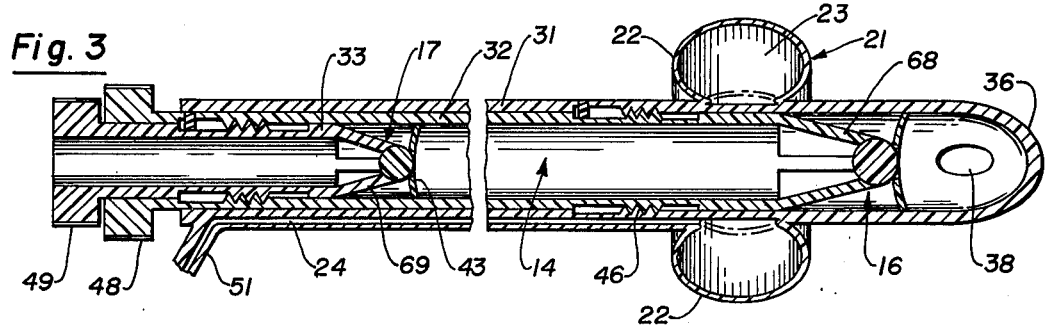
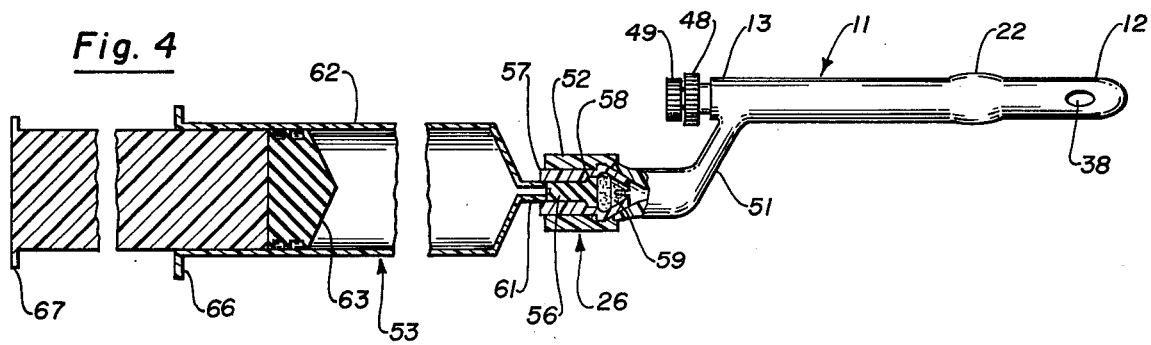
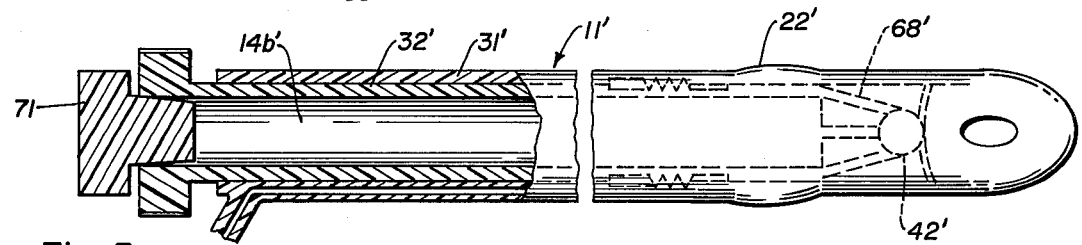

ARTIFICIAL URETHRA

BACKGROUND OF THE INVENTION

1. Field of Invention

The invention relates to urinary catheters used for draining the bladder of patients who cannot void or empty their bladders for various reasons, or may not be able to control their urinating.

2. Description of Prior Art

Three types of urinary catheters are in use. One is a straight rubber catheter which is inserted through the penis or female urethra, held in place until the bladder is empty and then removed. A second type is the so-called Foley rubber catheter which is fashioned with a balloon at the inner, inserted end which may be inflated after insertion for retention of the inner end of the catheter within the bladder, urine being continuously drained through the catheter for as long as is necessary. The outer, downstream end of the catheter is generally attached to a bag which may be carried by the patient or hung on the patient's bed. The Robinson catheter represents a modification of the simple Foley catheter in providing for infusion of solutions into the bladder as well as the urinary draining function. A third type known as a Condum catheter is commonly used with patients who do not have control of urination. In this type a prophylactic is drawn over the penis and is connected by a rubber tube to a bag which the patient carries or which may be hung on the patient's bed.

All of the prior art catheters have one problem in common, viz, frequency of infection. Whenever a catheter is placed into the bladder for urinal drainage, there is a very high incidence of infection. The Foley and Robinson catheters, if left in the patient for over a week, produce infection in practically 100% of the cases. The incidence of infection of just one single straight catheterization is as high as 1%.

Urinary infections are a tremendous everyday medical problem. Introduction of infection not only produces discomfort, fever and acute illness, but may eventually cause the kidneys to become infected and cease their function, a disease condition called chronic pyelonephritis.

SUMMARY OF INVENTION

The present invention provides access to the bladder which will not produce urinary tract infections and will represent a major innovation in the care and treatment of patients who require urinary drainage.

The major features and objects of the present invention include its prevention of infection, as above noted; elimination of the requirement of carrying a bag; the storage of urine in the bladder in a normal physiologic environment; providing patients with effective control over urination in a manner allowing normal physiologic urinating processes, e.g., permitting a adult male to stand up to a urinal, operate his catheter and urinate just like anyone else; and the ability to enable the precise measurement of urine storage in the bladder, as contrasted to a collecting bag or the like, where such procedure is indicated.

The invention possesses other objects and features of advantage, some of which of the foregoing will be set forth in the following description of the preferred form of the invention which is illustrated in the drawing accompanying and forming part of this specification. It is to be understood, however, that variations in the showing made by the said drawing and description may be adopted within the scope of the invention as set forth in the claims.

BRIEF DESCRIPTION OF THE DRAWING

Referring to said drawing:

FIG. 1 is an enlarged cross-sectional view of an artificial urethra constructed in accordance with the present invention and shown with the balloon part expanded as in catheter inserted position.

FIG. 2 is a view similar to FIG. 1 but with the parts in another position.

FIG. 3 is a view similar to FIGS. 1 and 2 but with the parts in a different position.

FIG. 4 is a side elevation of the device with an air inflating pump attached.

FIG. 5 is an enlarged view partially in corss section of a modified form of the device.

DETAILED DESCRIPTION OF INVENTION

The artificial urethra of the present invention comprises briefly a catheter 11 dimensioned for insertion through the urethra for positioning a distal end 12 of the catheter within the bladder and having a length providing an extracorporeal positioning of the outer end 13, the catheter being formed with a longitudinally extending bore 14 for passage of fluid between the bladder and bore 14; and closure means (see valves 16 and 17) mounted in longitudinally spaced relation in bore 14 and movable between positions opening and closing fluid passage through the bore and in closed position providing an air lock in the bore, see FIG. 3. As a feature of the present invention, means 18 (connected to valves 16 and 17) provide for selective opening and closing of the catheter passage enabling successive simultaneous opening of the closure means to permit bladder evacuation, see FIG. 1, closing of the inner, upstream closure 16 to seal off the bladder while leaving the outer downstream closure 17 in open position, see FIG. 2, for clearing fluid from bore 14, and closing of both closures 16 and 17 to establish the aforementioned air lock.

As a further feature of the present invention, an inflatable protuberance 21 is provided adjacent inner end 12 for retaining the catheter within the bladder. This protuberance may be formed as in the case of the conventional Foley catheter with an imperforate elastic wall 22 defining an expandable air chamber 23; a longitudinally extending air passage 24 communicating with chamber 23 and extending longitudinally of the catheter to adjacent outer end 13 for pressurizing and expanding chamber 13 and wall 22; and a check valve 26 mounted in the air passage for retaining the pressurized expanded shape of protuberance 21.

Preferably and as here shown, the catheter and valve structure are contructed of a plurality of concentric telescopically mounted tubular members 31, 32 and 33 having registering bores 14a, 14b and 14c, respectively, through which fluid may flow longitudinally of the catheter. Outer tubular member 31 is here formed with a closed rounded end 36 to facilitate insertion into and through the urethra and forms the inner or inserted end 12 of the catheter. End wall 36 is formed with one or more openings 38 providing fluid flow between the bladder and passage 14a. A valve seat 37 is provided within bore 14a on the downstream side of openings 38, seat 37 here comprising an interior transverse wall having a fluid passage 41 therethrough. Co-functioning with seat 37 is a valve part 42 which is carried at the inner end of tubular member 32 and is movable to and from seat 37 for opening and closing fluid flow through passage 41. A second valve seat 43, similar in construction to seat 37, is provided in bore 14b spaced downstream from of valve member 42 and seat 37; and a valve part 44 is carried at the inner end of tubular member 33 for movement to and from seat 43 for closing and opening the fluid flow therethrough.

Any convenient means may be provided for advancing the valve parts 42 and 44 to and from their respective seats. As here shown, such longitudinal displacement is conveniently effected by threadably attaching members 31 and 32, see engaged threads 46, so that relative rotation of member 32 wihtin member 31 will cause longitudinal displacement of valve part 42. In a like manner, longitudinal displacement of valve part 44 is here effected by threadably attaching tubular members 32 and 33, see engaged threads 47. As will be observed from the drawings, the outer ends of the tubular members are offset longitudinally at the outer end of the catheter so as to afford manual access and engagement and rotation of the individual members; and to facilitate such operation, enlarged handles or hand wheels 48 and 49 are provided on the outer ends of members 32 and 33, respectively.

Air passage 24 may be conveniently formed in the outer member 31 and connected by a branch conduit 51 to a combination fitting and check valve 52 adapted for connection to a manually actuated pump 53 of the type used in connection with the Foley catheter. Any type of check valve may be used. As here shown, a valve member 56 is mounted for reciprocation in a valve cylinder 57 for movement to and from a valve seat 58. An elastic pad 59 of porous material is mounted in cylinder 57 for urging valve 56 to its seat. Cylinder 57 also forms a socket for receipt of an end 61 of pump 53 so that air pressure delivered by the pump will displace valve 58 to open position, to the right as seen in the drawing, against the resilient resistance of pad 59, thereby causing air to flow longitudinally through passage 24 to pressurize and expand ballon chamber 23. Upon release of pressure from the pump, pad 59 and the air pressure will cause the return movement of valve 56 to its seated closed position. Pump 53 may simply comprise a cylinder 62 and manually displaceable plunger 63 therein, the cylinder and plunger being formed with finger engaging portions 66 and 67 for convenient operation.

In use the catheter with its balloon 22 deflated is inserted into and through the urethra of a patient to dispose the distal end 12 of the chatheter within the bladder. Balloon 22 is then inflated, as illustrated in FIGS. 1–3, so as to retain the catheter in place. Valves 16 and 17 normally will be closed in the position illustrated in FIG 3 so as to provide the desired air lock in passage 14, which effectively closes off the passage of infectious agents into the bladder. To evacuate the bladder, the user will rotate hand wheels 48 and 49 so as to back off valve parts 42 and 44 and open valves 16 and 17. In such condition there is a straight through passage from the inner to the outer ends of the catheter. On completion of evacuation, hand wheel 48 will be rotated to close valve 16 leaving valve 17 open. Thereafter fluid retained within the catheter may be shaken out. Finally, hand wheel 49 will be rotated to close valve 17 and reestablish the air lock.

In order to provide for the free flow of fluids through the catheter with the valves in open position, valve parts 42 and 44 are mounted to the proximal ends of tubular members 32 and 33 by skeleton or spider structures 68 and 69 permitting free fluid flow through the supporting structures.

The catheter may be made in different lengths and sizes for use with men, women and children; and should be made of nonreactive material, such as Silastic, Teflon or the like, permitting the retention of the catheter in the body for protracted periods.

A modified form of the invention is illustrated in FIG. 5 wherein the outer, downstream closure means 17 comprises a simple closure part, such as stopper 71 demountably positionable in the outer end of bore 14b' of the intermediate telescopic member 32'. In this embodiment of the invention, tubular member 33 and its valve part 44 are deleted entirely as well as valve seat 43, and these parts are replaced by a simple closure 71 for the outer end of passage 32'. Opening and closing of the outer end of the catheter is done simply by removing or inserting member 71. With the removal of valve seat 43 from member 32', bore 14b' is completely open and unimpeded throughout the full length of tubular member 32' from the outer end to the valve part 42' supported on a skeleton structure 68' at the inner end of the device. Accordingly, the structure premits the easy introduction of a long syringe into passage 14' for flushing out the interior of the catheter with a sanitizing fluid. During such sanitizing operation, valve 42' will be closed to prevent exposure of the bladder to any of the sanitizing fluid. Other than the changes herein noted, the structure of the catheter 11' is identical to the catheter 11 including the threadably attached tubular members 31' and 32', the inner, upstream closure means 16, the expandable balloon wall 22', etc.

What is claimed is:

1. An elongate, tubular urethra catheter having an inner end and an outer end and adapted for positioning in the urethra canal of a user and having a passage therethrough for providing periodic bladder drainage periods;

individually manually operable closure means supported on the catheter in spaced upstream and downstream positions for occluding the passage through the catheter at said positions; and
    means for sequentially operating the closure means to close the upstream closure means first and the downstream closure means second to provide a liquid and air seal in said passage at each of said positions and an air lock in said passage between said positions.

2. A device as defined in claim 12, said closure means comprising a pair of valves mounted in longitudinally spaced relation in said passage and individually movable between positions opening and closing the fluid passage; and said second named means mounted at the outer end of said catheter and connected to said valves for effecting selective opening and closing thereof, said valves in closed position providing said air lock.

3. A device as defined in claim 2, said second named means successively providing for opening of both valves to permit bladder evacuation, closing of the upstream valve to seal off the bladder while leaving the downstream valve open for clearing of fluid from said passage, and closing of the downstream valve to establish said air lock.

4. A device as defined in claim 1, said catheter comprising telescopically mounted tubular members, the outer of said members having a longitudinally extending bore and a valve seat therein adjacent its inner end;
   an inner of said members being mounted in said outer member bore and having a valve part movable into and out of engagement with said seat for controlling fluid flow therethrough, said valve seat and valve part providing one of said closure means; and
   a closure part demountably positionable in the outer end of said inner member bore and providing the other of said closure means.

5. A device as defined in claim 3, said catheter being formed with an imperforate elastic wall adjacent its inner end defining an expandable air chamber;
   third means providing an air passage communicating with said chamber and extending longitudinally of said catheter to adjacent the outer end thereof for pressurizing and expanding said chamber and wall into a protuberance for retaining said inner end in the bladder; and
   a check valve mounted in said air passage for retaining the pressurized expanded shape of said protuberance.

6. A device as defined in claim 5, said catheter comprising telescopically mounted tubular members, the outer of said members having a longitudinally extending bore and a valve seat therein adjacent its inner end;
   an inner of said members being mounted in said outer member bore and having a valve part movable into and out of engagement with said seat for controlling fluid flow therethrough, said inner member haing a longitudinally extending bore and a second valve seat therein proximally of said first valve seat; and
   a second valve part mounted in said inner member bore for movement to and from said second seat for controlling fluid flow therethrough.

7. A device urethra as defined in claim 5 and comprising a plurality of concentric, telescopically mounted and threadably attached tubular members having registered bores;
   the outer (first) of said members having a longitudinally extending bore and providing a fluid opening at the inner end of said catheter and having a first valve seat in its bore proximally of said opening;
   the adjacent interior (second) member having a valve part at its inner end movable to and from said seat for controlling fluid flow therethrough and having a longitudinally extending bore and a second valve seat in its bore proximally of said first valve seat;
   the next internal adjacent (third) member having a valve part at its inner end mobable to and from said second seat for controlling fluid flow therethrough; and
   said first and third means being connected to said second and third members for selective rotation thereof relative to said first and second members respectively to effect the described valving action.

8. A device as defined in claim 7, said valve parts being secured to thier respective members by structure permitting fluid flow through said structure.

9. A device as defined in claim 8, said second and third members being dimensioned to position their outer ends extracorpually, and said outer ends of said second and third members being offset longitudinally to provide individual manual engagement.

10. A device as defined in claim 9, and manually engageable handles provided on said outer ends of said second and third members.

11. A method of preventing infection in the artificial draining of human bladder comprising:
   disposing an elongate, tubular catheter having a passageway therethrough in the user's urethra for providing periodic bladder drainage periods, said catheter having separate spaced apart closure means located on and supported by the catheter and
   between said drainage periods, sequentially operating said closure means to close said catheter passageway first at an upstream closure position and second at a spaced downstream closure position to provide an air and liquid seal at said closure positions and an air lock therebetween.

* * * * *

UNITED STATES PATENT AND TRADEMARK OFFICE
CERTIFICATE OF CORRECTION

PATENT NO. : 4,026,298
DATED : May 31, 1977
INVENTOR(S) : Henry Grausz

It is certified that error appears in the above-identified patent and that said Letters Patent are hereby corrected as shown below:

Column 1, line 57, after "permitting", change "a" to ---an---.

Column 2, line 17, change "corss" to ---cross---.

Column 3, line 6, after "downstream from" delete "of".

Column 3, line 15, change "wihtin" to ---within---.

Column 3, line 53, after "distal" insert ---, inner---.

Column 4, line 27, change "premits" to ---permits---.

Claim 2, line 1, change "12" to ---1---.

Claim 6, line 9, change "haing" to ---having---.

Claim 7, line 1, after "A device" delete ---urethra---.

Claim 7, line 15, change "internal" to ---internally---.

UNITED STATES PATENT AND TRADEMARK OFFICE
CERTIFICATE OF CORRECTION

PATENT NO. : 4,026,298
DATED : May 31, 1977
INVENTOR(S) : Henry Grausz

It is certified that error appears in the above-identified patent and that said Letters Patent are hereby corrected as shown below:

Claim 7, line 16, change "mobable" to ---movable---.

Claim 9, line 3, change "extracorpually" to ---extracorpreally---.

Claim 11, line 7, after "supported by the catheter" insert ---;---.

Signed and Sealed this

Twentieth Day of December 1977

[SEAL]

Attest:

RUTH C. MASON
Attesting Officer

LUTRELLE F. PARKER
Acting Commissioner of Patents and Trademarks